(12) United States Patent
Gomi et al.

(10) Patent No.: US 9,540,344 B2
(45) Date of Patent: Jan. 10, 2017

(54) PRODUCTION METHOD FOR ISOQUINOLINE DERIVATIVES AND SALTS THEREOF

(71) Applicant: KOWA CO., LTD., Nagoya-shi (JP)

(72) Inventors: Noriaki Gomi, Higashimurayama (JP); Tadaaki Ohgiya, Tokorozawa (JP); Kimiyuki Shibuya, Tokorozawa (JP)

(73) Assignee: KOWA CO., LTD., Nagoya-shi (JP)

( * ) Notice: Subject to any disclaimer, the term of this patent is extended or adjusted under 35 U.S.C. 154(b) by 59 days.

(21) Appl. No.: 14/561,258

(22) Filed: Dec. 5, 2014

(65) Prior Publication Data

US 2015/0087824 A1 Mar. 26, 2015

Related U.S. Application Data

(62) Division of application No. 13/816,534, filed as application No. PCT/JP2011/069187 on Aug. 25, 2011, now Pat. No. 9,045,460.

(30) Foreign Application Priority Data

Aug. 26, 2010 (JP) .................................. 2010-189392

(51) Int. Cl.
*C07D 243/08* (2006.01)
*C07D 401/12* (2006.01)

(52) U.S. Cl.
CPC ........... *C07D 401/12* (2013.01); *C07D 243/08* (2013.01)

(58) Field of Classification Search
CPC .................................................. C07D 243/08
USPC ......................................................... 540/575
See application file for complete search history.

(56) References Cited

U.S. PATENT DOCUMENTS

| | | |
|---|---|---|
| 4,678,783 A | 7/1987 | Hidaka et al. |
| 5,945,415 A | 8/1999 | Kato et al. |
| 6,153,608 A | 11/2000 | Hidaka et al. |
| 2002/0010174 A1 | 1/2002 | Galley et al. |
| 2008/0021018 A1 | 1/2008 | Ohshima et al. |
| 2008/0064681 A1 | 3/2008 | Hidaka et al. |
| 2010/0069365 A1 | 3/2010 | Carniato et al. |
| 2012/0283247 A1 | 11/2012 | Carniato et al. |

FOREIGN PATENT DOCUMENTS

| | | |
|---|---|---|
| JP | 61 227581 | 10/1986 |
| JP | 9-100276 A | 4/1997 |
| JP | 11 171885 | 6/1999 |
| JP | 2003-534332 A | 11/2003 |
| JP | 2006 290827 | 10/2006 |
| JP | 2006 348028 | 12/2006 |
| JP | 2007-238458 | 9/2007 |
| JP | 2010-508312 A | 3/2010 |
| WO | 97 28130 | 8/1997 |
| WO | 99 20620 | 4/1999 |
| WO | 2006 057397 | 6/2006 |

OTHER PUBLICATIONS

International Search Report Issued Oct. 4, 2011 in PCT/JP11/69187 Filed Aug. 25, 2011.
The Extended European Search Report issued Aug. 2, 2013, in Application No. / Patent No. 11819992.6-2610252 PCT/JP2011069187.
Office Action issued Mar. 10, 2015 in Japanese Patent Application No. 2012-530708 (with English language translation).
Office Action issued Mar. 10, 2015 in Japanese Patent Application No. 2014-151680 (with English language translation).
Theodora W. Greene, et al. "Protective Groups in Organic Synthesis" John Wiley & Sons, Inc., Third Edition, 1999, pp. 518-523 and cover pages.
Toshiyuki Kan, et al. "Ns strategies: a highly versatile synthetic method for amines" Chemical Communications, No. 4, 2004, pp. 353-359.
Office Action issued Dec. 1, 2015 in Japanese Patent Application No. 2014-151680 (with English language translation).

*Primary Examiner* — Brenda Coleman
(74) *Attorney, Agent, or Firm* — Oblon, McClelland, Maier & Neustadt, L.L.P.

(57) ABSTRACT

The present invention provides a method capable of industrially producing a target product, i.e., a compound represented by the aforementioned formula (I) or a salt thereof, which is useful for preventing and treating cerebrovascular disorders such as cerebral infarction, cerebral hemorrhage, subarachnoid hemorrhage, and cerebral edema, particularly for preventing and treating glaucoma, at high yield even on a large scale without imposing a negative impact on the environment. The present invention provides a method for producing a compound represented by formula (I) or a salt thereof, wherein the method comprises a step of reacting a compound represented by formula (III) or a salt thereof with a compound represented by formula (II) in the presence of at least one solvent selected from the group consisting of a nitrile solvent, an amide solvent, a sulfoxide solvent, and a urea solvent, and a base.

3 Claims, No Drawings

PRODUCTION METHOD FOR ISOQUINOLINE DERIVATIVES AND SALTS THEREOF

CROSS-REFERENCE TO RELATED APPLICATIONS

This application is a divisional of U.S. application Ser. No. 13/816,534 filed Feb. 12, 2013, pending, which is a National Stage of PCT/JP2011/069187 filed Aug. 25, 2011 and claims the benefit of JP 2010-189392 filed Aug. 26, 2010.

TECHNICAL FIELD

The present invention relates to a method for producing an isoquinoline derivative or a salt thereof which is useful for preventing and treating cerebrovascular disorders such as cerebral infarction, cerebral hemorrhage, subarachnoid hemorrhage, and cerebral edema, particularly as a therapeutic drug for glaucoma.

BACKGROUND ART (S)-(−)-1-(4-Fluoroisoquinolin-5-yl)sulfonyl-2-methyl-1,4-diazepane is a compound represented by the following formula (1):

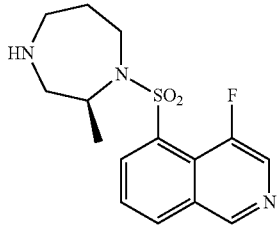

(1)

and particularly, the hydrochloride dihydrate of the above compound is a non-hygroscopic, water-soluble crystal with excellent chemical stability, for which it is known to be useful as a pharmaceutical product (see Patent Documents 1 and 2). These isoquinoline-5-sulfonamide compounds are known to be useful as preventive and therapeutic agents for cerebrovascular disorders such as cerebral infarction, cerebral hemorrhage, subarachnoid hemorrhage, and cerebral edema, particularly as preventive and therapeutic agents for glaucoma (see Patent Documents 1 to 5).

Conventionally, as the production method for the aforementioned compound, for example, a production method performed by the method described in Patent Document 1, which is illustrated by the following production process, is reported (Production method 1-A).

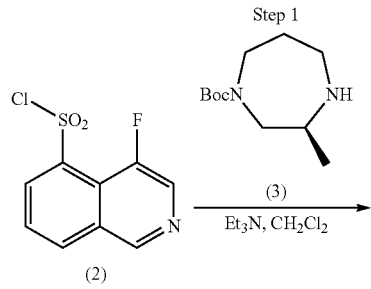

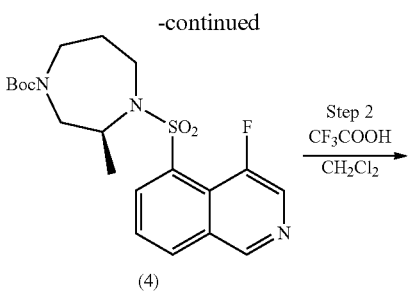

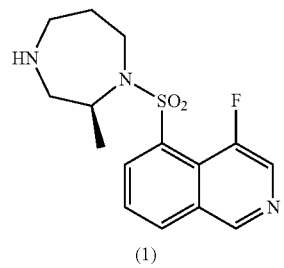

That is, it is a method for producing the desired compound (1) by synthesizing a compound (4) by reacting (S)-1-tert-butoxycarbonyl-3-methyl-1,4-diazepane (3) with 5-chlorosulfonyl-4-fluoroisoquinoline (2) in methylene chloride in the presence of triethylamine (Step 1), and then deprotecting the compound (4) thus obtained by adding trifluoroacetic acid in methylene chloride (Step 2).

Also, it is known that (S)-1-tert-butoxycarbonyl-3-methyl-1,4-diazepane (3), which is an important intermediate for the production of the aforementioned compound (1), can be produced by, for example, a method such as those shown below (production method 1-B; see Patent Document 1).

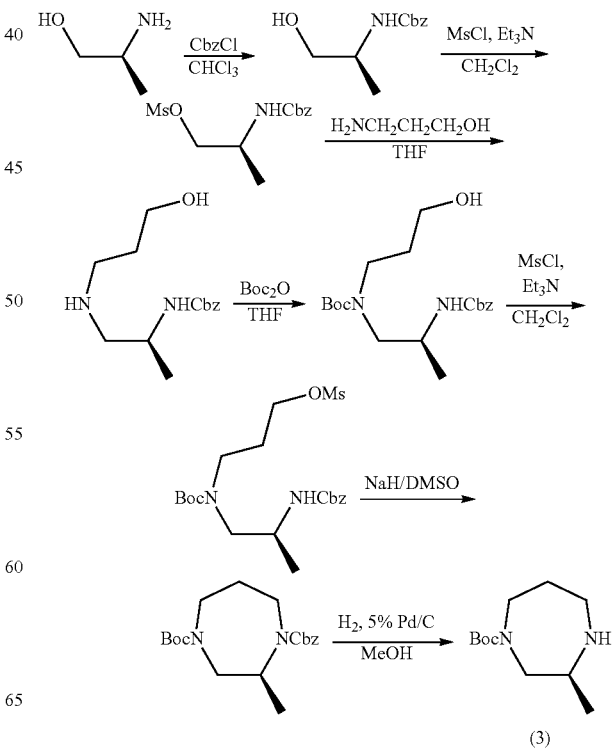

Also, meanwhile, it is known that the compound (1) can also be produced by a production pathway such as those shown below (production method 2) (see Patent Document 1).

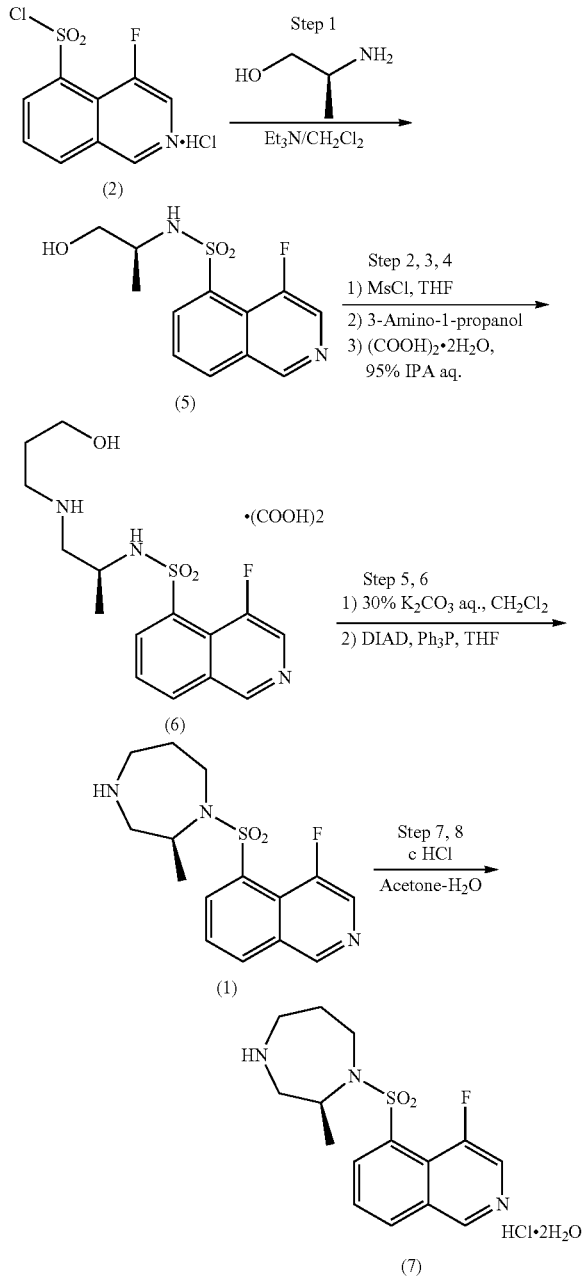

PRIOR ART LIST

Patent Document

Patent Document 1: International Publication No. WO1999/20620
Patent Document 2: International Publication No. WO2006/057397
Patent Document 3: International Publication No. WO1997/028130
Patent Document 4: JP-A-2006-348028
Patent Document 5: JP-A-2006-290827

SUMMARY OF THE INVENTION

Technical Problem

However, a problem was that although the aforementioned production method 1-A could be performed at small laboratory scale, from the viewpoint of industrial large scale production, a tremendous negative impact would be imposed on the environment due to the fact that the process for coupling the compounds (2) and (3) was performed in an environmentally harmful halogenated hydrocarbon solvent. In view of the above, solvents other than halogenated hydrocarbon solvents which are also listed in the specification of Patent Document 1, for example, dioxane and tetrahydrofuran were actually tested. As a result, a problem was revealed that while indeed the above coupling reaction proceeded partially, the reaction did not complete with the starting materials still left even by prolonging the reaction time, resulting in a yield of as low as 30%. Further, dioxane does not easily degrade in the environment, and not only that, but also its removal is difficult. Furthermore, dioxane is known as a compound which is irritating to humans and potentially causing damage to the brain, kidney, and liver. In view of the above, dioxane is not preferable.

Moreover, it was found that when the compound (3) was actually produced according to the aforementioned production method 1-B, acquisition of a good yield of the target compound with reproducibility was difficult. That is, although sodium hydride was used in dimethyl sulfoxide in the formation of the 1,4-diazepane ring in the above production pathway, when this process was actually carried out, a good yield of the target compound could not be obtained with reproducibility. It was also revealed that because this method involves a synthetic pathway via an unstable intermediate, the intermediate was easily converted into a different compound. This instability of the intermediate affects the reproducibility of the reaction, which exposed the underlying problem and limitation of this production process.

Meanwhile, various problems arose also when a large scale production by the aforementioned production method 2 was actually attempted. For example, by-products, which were formed at each step in the linear production method involving eight steps, were accumulated as impurities at each step, giving a more complex impurity profile. Accordingly, complex recrystallization had to be repeated to purify a product until reaching the requisite of a purity level for a pharmaceutical product, and even if the laboratory yield was good, the total yield was markedly decreased in actual large scale production, revealing that the aforementioned production method 2 lacked industrial utility value in a true sense. Considering these problems from the viewpoint of GMP process control, which is required for pharmaceutical production, they can be sorted out as follows.

1) A number of complex control processes involving as many as eight steps are required, 2) regioisomers which are difficult to remove are present in the step of reacting 3-amino-1-propanol in Step 3, 3) crystallization purification by oxalate is needed for removal of regioisomer impurities in Step 4, 4) water is mixed in by the liquid separation and extraction operation, which is performed to convert oxalate back into free base in Step 5, 5) moisture control is necessary in the Mitsunobu reaction for ring-closure of the compound (6) into the compound (1) in Step 6, 6) deviation control such as addition of reagents becomes necessary due to poor reproducibility of ring-closure reaction, and 7) complex purification is necessary for removal of impurities after the Mitsunobu reaction in Step 7, leading to a reduced isolated yield. These are the problems which need to be solved for a stable supply of active pharmaceutical ingredient, which are required to have high chemical purity.

Accordingly, the present invention relates to provision of a novel method for producing an isoquinoline derivative comprising the compound represented by the aforementioned formula (1) or a salt thereof at high purity and high yield with good reproducibility in an environmentally-friendly, simple manner.

Solution to Problem

In view of the foregoing, the present inventors conducted an intensive study. As a result, they have found that, in the production process of the final target product shown by the following formulae,

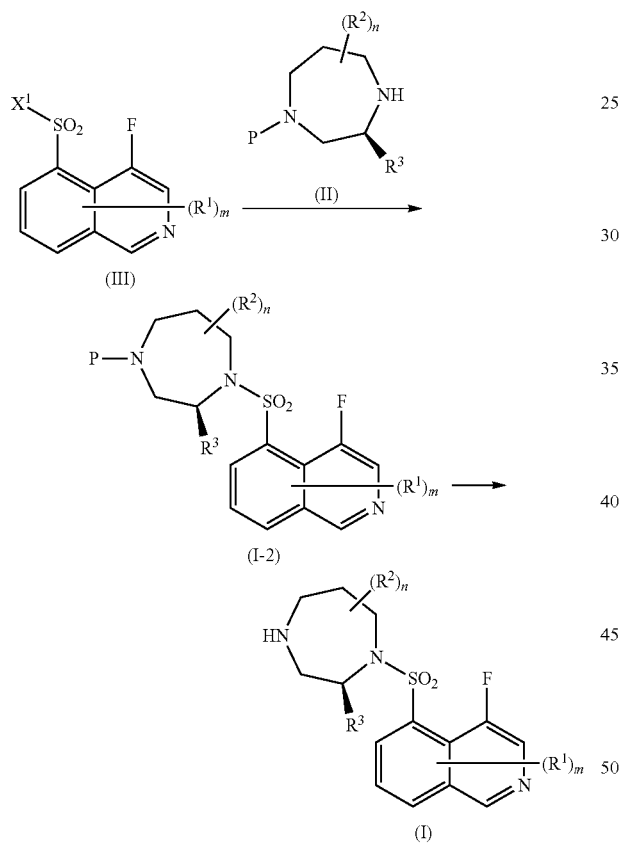

(wherein, $X^1$ represents fluorine, chlorine, bromine, or iodine, $R^1$, $R^2$, and $R^3$ may be the same or different and each represents a $C_{1-4}$ alkyl group, P represents a protecting group, m represents an integer of 0 to 3, and n represents an integer of 0 to 3)

a solvent which can be favorably used in the process for coupling the compounds (II) and (III) is a nitrile solvent, an amide solvent, a sulfoxide solvent, or a urea solvent, and they can be instantly converted into the target product in an almost quantitative manner by using the above solvents. The use of these solvents eliminates the necessity of using halogenated hydrocarbon solvents, which impose a tremendous negative impact on the environment, and allows the coupling process to be performed on a large scale with maintaining high yield. Further, they have found that, considering post-reaction treatment such as removal of solvents, acetonitrile is the most suitable among those solvents. They have further found that also in the process of deprotection the use of hydrochloric acid in an ethyl acetate solvent allows isolation of the target compound (I) as hydrochloride crystal, whereby the target compound (I) can be obtained by a simpler operational procedure without complex solvent-removal operation. Further, since there is no need to use any halogenated hydrocarbon solvent in the above deprotection process, there is no risk of environmental contamination.

The present inventors have further found that, in a large scale production of the compound (II), which is an important intermediate in the coupling process, a compound can be converted into the target compound at higher purity and higher yield with better reproducibility in comparison with conventional methods. That is, the present method has enabled elimination of production in an environmentally harmful halogenated hydrocarbon solvent and conversion of a compound into each intermediate at high purity and high yield. Further, they have successfully obtained the desired target compound while cutting off one step from the whole production process without loosing the optical purity, by performing the Mitsunobu reaction using a nosyl group instead of a carbobenzyloxy group as a protecting group to enable a ring-closure reaction to take place under milder conditions for the purpose of avoiding a variety of problems emerging in a reaction in which sodium hydride is used in dimethyl sulfoxide in the formation of the 1,4-diazepane ring.

That is, the present invention relates to the following.

[1] A method for producing a compound represented by formula (I) or a salt thereof:

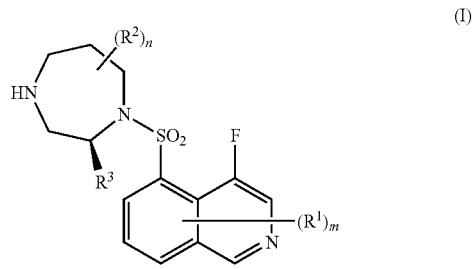

wherein $R^1$ represents a $C_{1-4}$ alkyl group, $R^2$ and $R^3$ can be the same or different and each represents a $C_{1-4}$ alkyl group, m represents an integer of 0 to 3, and n represents an integer of 0 to 3 the method comprising a step of reacting a compound represented by formula (III) or a salt thereof:

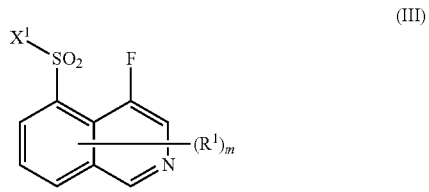

wherein $X^1$ represents fluorine, chlorine, bromine, or iodine, $R^1$ and m are the same as described above
with a compound represented by formula (II):

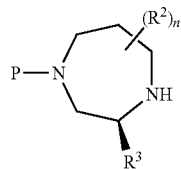

wherein $R^2$, $R^3$, and n are the same as described above, P represents a $C_{1-6}$ alkoxycarbonyl group, a $C_{6-10}$ aryl $C_{1-3}$ alkyl group, or a $C_{6-10}$ aryl $C_{1-3}$ alkoxycarbonyl group in the presence of at least one solvent selected from the group consisting of a nitrile solvent, an amide solvent, a sulfoxide solvent, and a urea solvent, and a base.

[2] The method according to the aforementioned [1], wherein m and n in the aforementioned formulae (I), (II), and (III) are 0 respectively.

[3] The method according to the aforementioned [1] or [2], wherein $R^3$ in the aforementioned formulae (I), (II), and (III) is a methyl group.

[4] The method according to any one of the aforementioned [1] to [3], wherein the aforementioned solvent is at least one solvent selected from the group consisting of N,N-dimethylformamide, dimethylsulfoxide, N-methylpyrrolidone, N,N-dimethylpropyleneurea, and acetonitrile.

[5] The method according to any one of the aforementioned [1] to [4], wherein the aforementioned solvent is acetonitrile.

[6] The method according to any one of the aforementioned [1] to [5], wherein an amount of the aforementioned solvent is 1 to 40 times the amount (v/w) of a compound represented by the aforementioned formula (III).

[7] The method according to any one of the aforementioned [1] to [6], wherein the aforementioned base is a tertiary amine.

[8] The method according to any one of the aforementioned [1] to [7], further comprising a step of producing a compound represented by formula (IV):

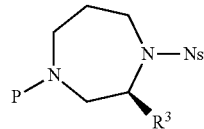

wherein $R^3$ represents a $C_{1-4}$ alkyl group, Ns represents a nosyl group, and P represents a $C_{1-6}$ alkoxycarbonyl group, a $C_{6-10}$ aryl $C_{1-3}$ alkyl group, or a $C_{6-10}$ aryl $C_{1-3}$ alkoxycarbonyl group by reacting a compound represented by formula (V):

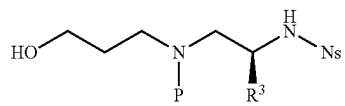

wherein $R^3$, Ns, and P are the same as described above
in a solvent in the presence of a phosphine reagent and an azo reagent.

[9] The method according to the aforementioned [8], wherein the aforementioned phosphine reagent is triphenylphosphine and the aforementioned azo reagent is diisopropyl azodicarboxylate.

[10] The method according to any one of the aforementioned [1] to [7], further comprising a step of producing a compound represented by formula (II-3):

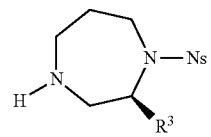

wherein $R^3$ represents a $C_{1-4}$ alkyl group and Ns represents a nosyl group,
by reacting a compound represented by formula (VI):

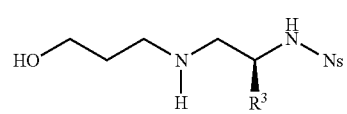

wherein, $R^3$ and Ns are the same as described above,
in a solvent in the presence of a phosphine reagent and an azo reagent.

[11] The method according to the aforementioned [10], wherein the aforementioned phosphine reagent is triphenylphosphine and the aforementioned azo reagent is diisopropyl azodicarboxylate.

[12] The method according to the aforementioned [10] or [11], further comprising a purification step using cation exchange resin.

[13] The method according to any one of the aforementioned [1] to [9], further comprising a step of deprotecting a tert-butoxycarbonyl group of a compound represented by formula (I-3):

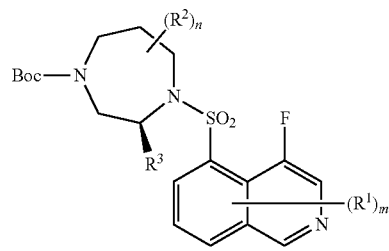

wherein, $R^1$, $R^2$, and $R^3$ can be the same or different and respectively represents a $C_{1-4}$ alkyl group, m represents an integer of 0 to 3, n represents an integer of 0 to 3, and Boc represents a tert-butoxycarbonyl group,
in a mixed solvent of at least one solvent selected from the group consisting of methyl acetate, ethyl acetate, and propyl acetate, and hydrochloric acid.

Effects of the Invention

According to the present invention, a compound represented by the aforementioned formula (I) or a salt thereof, which is useful for preventing and treating cerebrovascular disorders such as cerebral infarction, cerebral hemorrhage, subarachnoid hemorrhage, and cerebral edema, particularly for preventing and treating glaucoma, can be produced at high yield and high purity even on a large scale without imposing a negative impact on the environment. Specifically, in the reaction for coupling the compounds represented by the aforementioned formulae (II) and (III), the target product can be produced at high yield and high purity even on a large scale without imposing a negative impact on the environment, and in the production of the compound represented by the aforementioned formula (II), the target product can be produced at high yield even on a large scale.

EMBODIMENTS FOR CARRYING OUT THE INVENTION

Hereinbelow, the present invention will be described in detail.

[Production Method]

The compound represented by the formula (I) or a salt thereof according to the present invention can be produced by the methods illustrated by the following synthetic pathways 1 and 2. It should be noted that functional groups may be protected in each reaction as needed, and as to the protection and deprotection conditions, protection and deprotection can be performed with reference to a generally employed method (Protective Groups in Organic Synthesis Third Edition, John Wiley & Sons, Inc.).

Synthetic Pathway 1

Synthesis of 1,4-Diazepane Derivative

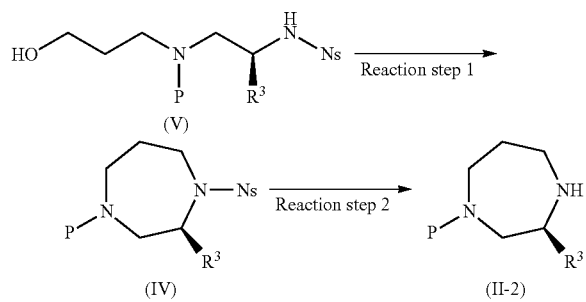

wherein each symbol has the same meaning as above.

Synthetic Pathway 2

Synthesis of the Final Compound

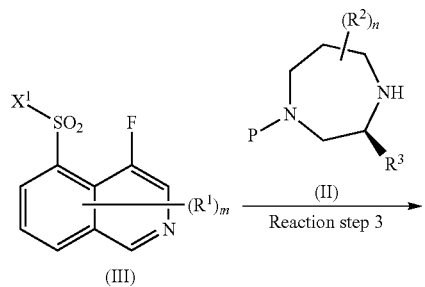

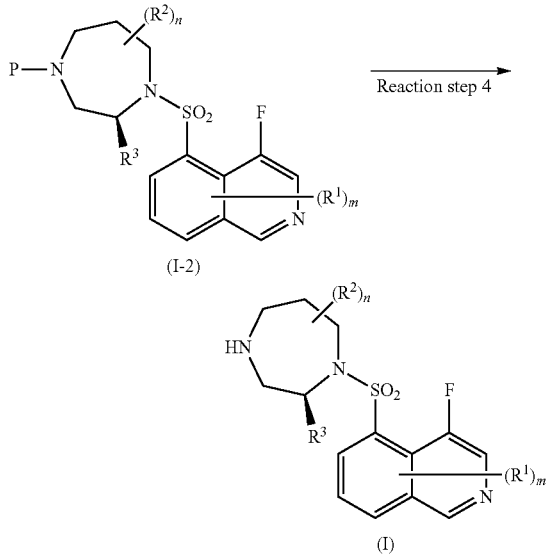

wherein each symbol has the same meaning as above.

Examples of the $C_{1-4}$ alkyl group defined by $R^1$, $R^2$ and $R^3$ include a methyl group, an ethyl group, an n-propyl group, an isopropyl group, a butyl group, an isobutyl group, a sec-butyl group, and a tert-butyl group. In the synthetic pathways 1 and 2, P is, for example, a $C_{1-6}$ alkoxycarbonyl group, a $C_{6-10}$ aryl $C_{1-3}$ alkyl group, or a $C_{6-10}$ aryl $C_{1-3}$ alkoxycarbonyl group. Here, examples of the $C_{1-6}$ alkoxycarbonyl group include a methoxycarbonyl group, an ethoxycarbonyl group, and a tert-butoxycarbonyl group (Boc). Examples of the $C_{6-10}$ aryl $C_{1-3}$ alkyl group include a benzyl group. Examples of the $C_{6-10}$ aryl $C_{1-3}$ alkoxycarbonyl group include a benzyloxycarbonyl group. Although m and n each represents an integer of 0 to 3, both of them are preferably 0. Also, particularly, $R^3$ is preferably a methyl group.

[Reaction Step 1]

Reaction step 1 can be performed by reacting the compound (V) in a solvent in the presence of a phosphine reagent and an azo reagent. Here, as the phosphine reagent, for example, trialkylphosphines such as trimethylphosphine, triethylphosphine, tripropylphosphine, triisopropylphosphine, tributylphosphine, triisobutylphosphine, and tricyclohexylphosphine, and triarylphosphines such as triphenylphosphine can be used. As the azo reagent, for example, diethyl azodicarboxylate (DEAD), diisopropyl azodicarboxylate (DIAD), di-tert-butyl azodicarboxylate (DBAD), 1,1-(azodicarbonyl)piperidine (ADDP), 1,1'-azobis(N,N'-diisopropylformamide) (TIPA), and 1,6-dimethyl-1,5,7-hexahydro-1,4,6-tetrazocine-2,5-dione (DHAD) can be used. Further, an ethylene dicarboxylic acid reagent can also be used in place of the azo reagent. As the ethylene dicarboxylic acid reagent, for example, dimethyl maleate, diethyl maleate, dimethyl fumarate, and diethyl fumarate can be used. As the solvent, for example, an ether solvent such as tetrahydrofuran, diethyl ether, and cyclopentyl methyl ether, an aromatic hydrocarbon solvent such as benzene, toluene, and xylene, an alcoholic solvent such as methanol and ethanol, an amide solvent such as dimethylformamide and dimethylacetamide, a nitrile solvent such as acetonitrile and propionitrile can be used alone or in combination.

As the phosphine reagent, triarylphosphines are preferably used, and particularly, triphenylphosphine is preferably used. Also, as the azo reagent, diisopropyl azodicarboxylate (DIAD) is preferably used. The amount of the phosphine reagent used in the reaction is preferably 1.1 to 1.6 molar equivalents relative to the compound (V). The amount of the azo reagent used in the reaction is preferably 1.1 to 1.6 molar equivalents relative to the compound (V). As the solvent, an ether solvent is preferably used, and particularly, tetrahydrofuran is preferably used. Although the amount of the solvent which can be used in this process is not particularly limited, it is 5 to 15 times the amount (v/w) of the compound (V). Although the reaction conditions are not particularly limited, this reaction can be performed, for example, at room temperature for 2 to 26 hours. This step can produce a high yield of the target compound even when production is carried out on a large scale. "Large scale" as referred to herein is not particularly strictly limited; however, it refers to a case in which the target compound is obtained in an amount of, for example, 500 g or more, preferably 1 kg or more, and more preferably 5 kg or more.

The raw material compound (V) can be produced in accordance with the method described in Patent Document 1. That is, it can be produced in accordance with, for example, the following reaction formulae.

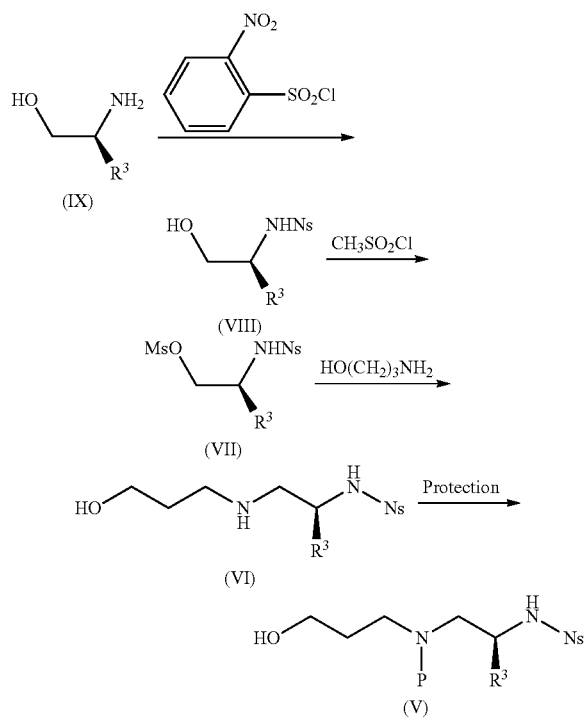

wherein $R^3$, P, and Ns have the same meaning as above. Ms represents a mesyl group.

In the presence of a base, 2-nitrobenzenesulfonyl chloride is reacted with the compound (IX) to convert it into a nosylamide compound (VIII), with which methanesulfonyl chloride is reacted to give a mesyl compound (VII). With this mesyl compound (VII), 3-aminopropanol is reacted, and further, the amino group is protected, whereby the compound (V) can be produced.

[Reaction Step 2]

In Reaction step 2, the compound (II-2) can be produced by deprotecting the compound (IV) through the action of a thiol compound in the presence of a weak base and a solvent.

The thiol compound which can be used in the reaction is not particularly limited, and examples thereof include thiophenol, 1-dodecanethiol, and thioglycolic acid. Unlike thiophenol, 1-dodecanethiol does not emit foul odor, and thus can be preferably used. Although the amount of the thiol compound is not particularly limited, normally, a molar equivalent or excess amount relative to the compound (IV) can be used. The weak base which can be used in the reaction is not particularly limited and examples thereof include alkali metal hydrogen carbonate such as potassium hydrogen carbonate and sodium bicarbonate, alkali metal carbonate such as potassium carbonate, sodium carbonate, and cesium carbonate, and an organic base such as triethylamine and diisopropylethylamine. The amount of the weak base is not particularly limited, but normally, it is 1.5 to 2.0 molar equivalents relative to the compound (IV).

As the solvent, for example, an ether solvent such as tetrahydrofuran and diethyl ether, an alcoholic solvent such as methanol and ethanol, a nitrile solvent such as acetonitrile and propionitrile, and water can be used alone or in combination. Among them, acetonitrile is preferably used. The amount of the solvent which can be used in the reaction is preferably 5 to 15 times the amount (v/w) of the compound (IV). Although the reaction conditions are not particularly limited, this reaction can be performed, for example, at room temperature to 60° C. for 1 to 24 hours.

Here, deprotection in this step 2 can be performed in accordance with the methods described in a publicly known literature or book (for example, Protective Groups in Organic Synthesis Forth Edition, John Wiley & Sons, Inc.) other than the method described above.

[Reaction Step 3]

Reaction step 3 is a reaction for coupling the compound (III) or a salt thereof and the compound (II) in the presence of a base and a solvent. In this step, an environmentally-friendly solvent capable of efficiently carrying out the reaction is used. The solvent which can efficiently carry out the reaction in this step is a nitrile solvent such as acetonitrile, propionitrile, or butyronitrile, an amide solvent such as N,N-dimethylformamide (DMF), dimethylacetamide (DMA), and N-methylpyrrolidone (NMP), a sulfoxide solvent such as dimethyl sulfoxide (DMSO), a urea solvent such as N,N-dimethylpropyleneurea (DMPU). Among these solvents, considering post-reaction treatment such as removal of solvents, a nitrile solvent, particularly acetonitrile is preferably used. When a solvent other than those described above, for example, the solvent described in Patent Document 1 is used, even if the target product could be produced at high yield at a small-scale laboratory level, problems arising on a large scale are distillation of solvents and markedly reduced yield. Also, as will be demonstrated in Test Example 1 to be described later, another problem is that the use of a solvent other than those described above leads to markedly reduced reaction efficiency. Further, yet another problem is that although the target product can be obtained at high yield even on a large scale when methylene chloride is used, a tremendous negative impact is imposed on the environment. The amount of the solvent used in the reaction is preferably 1 to 40 times the amount (v/w), more preferably 5 to 15 times the amount (v/w) of the compound (III). The reaction proceeds most efficiently when the solvent is used in an amount of about ten times the amount (v/w) of the compound (III).

Examples of the base which can be used include an organic base such as pyridine, collidine, lutidine, triethylamine, and diisopropylethylamine, and an inorganic base such as alkali metal hydride such as lithium hydride, sodium hydride, and potassium hydride, alkali metal hydrogen carbonate such as potassium hydrogen carbonate and sodium bicarbonate, alkali metal carbonate such as potassium carbonate and sodium carbonate, alkali metal hydroxide such as potassium hydroxide, sodium hydroxide, and lithium hydroxide. Preferred examples include an organic base, and more preferred examples include tertiary amine such as triethylamine. The amount of base to be used in the reaction is not particularly limited and is normally 1.5 to 3.0 molar equivalents relative to the compound (III). Although the reaction conditions are not particularly limited, a reaction condition of 0° C. to 10° C. for 1 to 3 hours is sufficient. More specifically, this step can be completed by carrying out a reaction for 1 to 3 hours while ice cooling. This reaction can also be performed by stirring for 30 minutes to one hour while ice cooling and then carrying out a reaction for 10 to 15 hours at room temperature. This step can produce a high yield of the target compound even when production is carried out on a large scale. "Large scale" as referred to herein is not particularly strictly limited; however, it refers to a case in which the target compound is obtained in an amount of, for example, 100 g or more, preferably 300 g or more, and more preferably 1 kg or more.

[Reaction Step 4]

Reaction step 4 is a step for deprotecting the compound (I-2) to produce the compound (I). The deprotection reaction is preferably carried out by reacting an acid with the compound (I-2). The acid which can be used in the reaction is not particularly limited and examples thereof include an inorganic acid such as hydrochloric acid and sulfuric acid and an organic acid such as formic acid and trifluoroacetic acid. Although the amount of the acid is not particularly limited, normally, a molar equivalent or excess amount relative to the compound (I-2) can be used. As the solvent, for example, an ether solvent such as tetrahydrofuran and diethyl ether, an alcoholic solvent such as methanol and ethanol, a nitrile solvent such as acetonitrile and propionitrile, an ester solvent such as methyl acetate, ethyl acetate, and propyl acetate, and water can be used alone or in combination. The amount of the solvent to be used in the reaction is preferably 5 to 25 times the amount (v/w) of the compound (I-2). A combination of hydrochloric acid and ethyl acetate is particularly preferable. Although the reaction conditions are not particularly limited, this reaction can be performed, for example, for 10 minutes to 3 hours while ice cooling.

Here, deprotection in this step 4 can be performed in accordance with the methods described in a publicly known literature or book (for example, Protective Groups in Organic Synthesis Forth Edition, John Wiley & Sons, Inc.). For example, deprotection can be performed by a method of deprotection using an acid or by hydrogenolysis as described in the above literature, etc.

Synthetic Pathway 3

Synthesis of 1,4-Diazepane Derivative (Alternative Route)

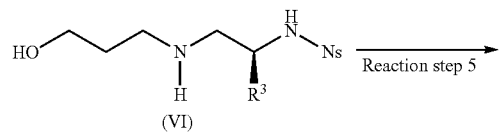

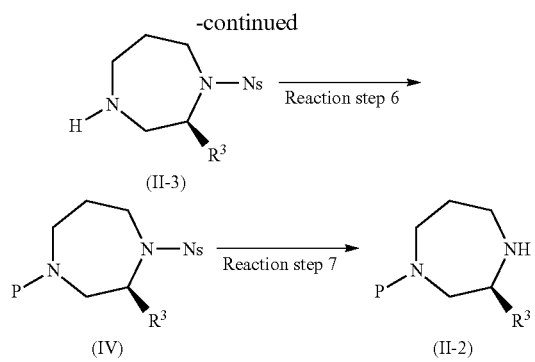

wherein each symbol has the same meaning as above.

[Reaction Step 5]

Reaction step 5 can be performed by reacting the compound (VI) in a solvent in the presence of a phosphine reagent and an azo reagent. Here, as the phosphine reagent, for example, the phosphine reagents which are listed in the aforementioned Reaction step 1, and the like can be used. As the azo reagent, for example, the azo reagents which are listed in the aforementioned Reaction step 1, and the like can be used. Further, an ethylene dicarboxylic acid reagent can also be used in place of the azo reagent. As the ethylene dicarboxylic acid reagent, for example, the ethylene dicarboxylic acid reagents which are listed in the aforementioned Reaction step 1, and the like can be used. As the solvent, for example, an ether solvent such as tetrahydrofuran, diethyl ether, and cyclopentyl methyl ether, an aromatic hydrocarbon solvent such as benzene, toluene, and xylene, an alcoholic solvent such as methanol and ethanol, and an amide solvent such as dimethylformamide and dimethylacetamide can be used alone or in combination.

As the phosphine reagent, triarylphosphines are preferably used, and particularly, triphenylphosphine is preferably used. Also, as the azo reagent, diisopropyl azodicarboxylate (DIAD) is preferably used. The amount of the phosphine reagent used in the reaction is preferably 1.1 to 1.6 molar equivalents relative to the compound (VI). The amount of the azo reagent used in the reaction is preferably 1.1 to 1.6 molar equivalents relative to the compound (VI). As the solvent, an ether solvent is preferably used, and particularly, tetrahydrofuran is preferably used. Although the amount of the solvent which can be used in this step is not particularly limited, it is 5 to 15 times the amount (v/w) of the compound (VI). Although the reaction conditions are not particularly limited, this reaction can be performed, for example, at 5° C. or below for 2 to 26 hours. This step can produce a high yield of the target compound even when production is carried out on a large scale. "Large scale" as referred to herein is not particularly strictly limited; however, it refers to a case in which the target compound is obtained in an amount of, for example, 500 g or more, preferably 1 kg or more, and more preferably 5 kg or more. Meanwhile, in order to obtain a high yield of the target compound (II-3) on a large scale, the compound (II-3) is preferably purified by an acid type cation exchange resin upon completion of the reaction in this step. Although the cation exchange resin which can be used is not particularly limited, examples thereof include Amberlyst 15™ (the product of The Dow Chemical Company), DIAION™ RCP160M (the product of Mitsubishi Chemical Corporation), and DOWEX™ MAC-3 (the product of The Dow Chemical Company). Regardless whether the aforementioned cation exchange resins are strong acid type or weak acid type, any of them can be used as long as it is an acid type cation exchange resin.

[Reaction Step 6]

Reaction step 6 is a step for protecting the amino group of the compound (II-3) to produce the compound (IV). The protection reaction can be performed by reacting a protecting reagent with the compound (II-3) in the presence of a base. The protecting reagent for the amino group of the compound (II-3) is not particularly limited as long as it is a reagent which gives a protecting group represented by the aforementioned P, i.e., a $C_{1-6}$ alkoxycarbonyl group, a $C_{6-10}$ aryl $C_{1-3}$ alkyl group, or a $C_{6-10}$ aryl $C_{1-3}$ alkoxycarbonyl group, and examples thereof include di-tert-butyl dicarbonate and benzyl chloroformate. A base which can be used in a reaction with these protecting reagents is not particularly limited, and examples thereof include potassium carbonate, pyridine, and triethylamine. Although the amount of the protecting reagent is not particularly limited, normally, a molar equivalent or excess amount relative to the compound (II-3) can be used. Also, although the amount of the base is not particularly limited, normally, a molar equivalent or excess amount relative to the compound (II-3) can be used. As the solvent, for example, an ether solvent such as tetrahydrofuran and diethyl ether, an alcoholic solvent such as methanol and ethanol, a nitrile solvent such as acetonitrile and propionitrile, an ester solvent such as methyl acetate, ethyl acetate, and propyl acetate, and water can be used alone or in combination. The amount of the solvent to be used in the reaction is preferably 5 to 25 times the amount (v/w) of the compound (II-3). Although the reaction conditions are not particularly limited, this reaction can be performed, for example, at 5° C. or below for 10 minutes to 6 hours.

Here, protection in this step 6 can be performed in accordance with the methods described in a publicly known literature or book (for example, Protective Groups in Organic Synthesis Forth Edition, John Wiley & Sons, Inc.).

[Reaction Step 7]

In Reaction step 7, the compound (II-2) can be produced by deprotecting the compound (IV) through the action of a thiol compound in the presence of a weak base and a solvent. The thiol compound which can be used in the reaction is not particularly limited, and examples thereof include thiophenol, 1-dodecanethiol, and thioglycolic acid. Unlike thiophenol, 1-dodecanethiol does not emit foul odor, and thus can be preferably used. Although the amount of the thiol compound is not particularly limited, normally, a molar equivalent or excess amount relative to the compound (IV) can be used. The weak base which can be used in the reaction is not particularly limited, and examples thereof include alkali metal hydrogen carbonate such as potassium hydrogen carbonate and sodium bicarbonate, alkali metal carbonate such as potassium carbonate, sodium carbonate, and cesium carbonate, and an organic base such as triethylamine and diisopropylethylamine. Although the amount of the weak base is not particularly limited, normally, it is 1.5 to 2.0 molar equivalents relative to the compound (IV).

As the solvent, for example, an ether solvent such as tetrahydrofuran and diethyl ether, an alcoholic solvent such as methanol and ethanol, a nitrile solvent such as acetonitrile and propionitrile, and water can be used alone or in combination. Among them, acetonitrile is preferably used. The amount of the solvent to be used in the reaction is preferably 5 to 15 times the amount (v/w) of the compound (IV).

Although the reaction conditions are not particularly limited, this reaction can be performed, for example, at room temperature to 60° C. for 1 to 24 hours.

Here, deprotection in this step 7 can be performed in accordance with the methods described in a publicly known literature or book (for example, Protective Groups in Organic Synthesis Forth Edition, John Wiley & Sons, Inc.) other than the method described above.

Although the salt of the compound (I) or (III) is not particularly limited, examples thereof include a conjugate salt of an inorganic acid such as hydrochloric acid, hydrobromic acid, hydriodic acid, sulfuric acid, nitric acid, and phosphoric acid or a conjugate salt of an organic acid such as formic acid, acetic acid, propionic acid, oxalic acid, malonic acid, succinic acid, fumaric acid, maleic acid, lactic acid, malic acid, tartaric acid, citric acid, methanesulfonic acid, ethanesulfonic acid, p-toluenesulfonic acid, aspartic acid, and glutamic acid. Particularly, as the salt of the compound (I) according to the present invention, a hydrochloride is preferable.

An intermediate and target product obtained by each of the aforementioned reactions can be isolated or purified, as needed, by subjecting them to a purification method routinely employed in synthetic organic chemistry such as filtration, extraction, washing, drying, concentration, recrystallization, and a variety of chromatographic techniques. Also, an intermediate can be used in the subsequent reaction without particularly purifying it.

Further, various kinds of isomers can be isolated by applying a routine procedure utilizing differences in physicochemical properties between isomers. A racemic mixture can be separated into the optically pure isomers by, for example, general racemic resolution methods such as an optical resolution method involving converting a racemic mixture into diastereomeric salts of general optically active acid such as tartaric acid or a method using optically active column chromatography. Also, a diastereomeric mixture can be separated by, for example, fractional crystallization or a variety of chromatographic techniques. Further, an optically active compound can also be produced by using appropriate optically active raw materials.

EXAMPLES

Hereinbelow, the present invention will be specifically described with reference to Examples and Test Examples; however, the present invention is not limited in any way by these Examples. It should be noted that the abbreviations used in the Examples below have the following meanings.

s: Singlet d: Doublet t: Triplet q: Quartet m: Multiplet br: Broad

J: Coupling constant

Hz: Hertz $CDCl_3$: Chloroform-d

DMSO-$d_6$: Dimethylsulfoxide-$d_6$ $^1$H-NMR: Proton nuclear magnetic resonance spectrum % ee: Enantiomeric excess TLC: Thin layer chromatography

Example 1

Production method of (S)-4-[(4-fluoroisoquinolin-5-yl)sulfonyl]-3-methyl-1,4-diazepane (i) Production of (S)—N-(1-hydroxypropan-2-yl)-2-nitrobenzenesulfonamide To a solution of (S)-(+)-2-amino-1-propanol (2.6 kg, 35 mol) in purified water (10.5 L) was added sodium bicarbonate (4.4 kg, 52 mol). To the resulting mixture was added a solution of 2-nitrobenzenesulfonyl chloride (7.3 kg, 33 mol) in tetrahydrofuran (10.2 L) at an internal temperature of −8° C. to −6° C. Subsequently, the resulting reaction mixture was stirred at room temperature for 39 hours. After confirming the disappearance of 2-nitrobenzenesulfonyl chloride by TLC, the mixture was filtered. The filtrate was then extracted with ethyl acetate, and the resulting organic layer was washed with saturated brine, dried over magnesium sulfate, and filtered. The filtrate was then concentrated under reduced pressure. The residue thus obtained was crystallized from petroleum ether/ethyl acetate to give the target product as a white solid (7.5 kg, yield 82.4%).

$^1$H-NMR (CDCl$_3$) δ: 1.14 (3H, d, J=6.8 Hz), 1.85 (1H, br s), 3.47-3.66 (3H, m), 5.48 (1H, d, J=6.8 Hz), 7.72-7.79 (2H, m), 7.86-7.92 (1H, m), 8.15-8.20 (1H, m). melting point: 82-83° C.

(ii) Production of (S)—N-(1-methanesulfonyloxypropan-2-yl)-2-nitrobenzenesulfonamide To a solution of (S)—N-(1-hydroxypropan-2-yl)-2-nitrobenzenesulfonamide (6.20 kg, 23.8 mol) in methylene chloride (32 L) was added 4-methylmorpholine (3.13 kg, 30.9 mol) at an internal temperature of 10° C. or below. The resulting reaction mixture was cooled to 0° C., and added a solution of methanesulfonyl chloride (3.27 kg, 28.5 mol) in methylene chloride (2 L) at an internal temperature of −5° C. to 0° C. Subsequently, the reaction mixture was stirred at room temperature for 20 hours. After confirming the disappearance of the starting materials by TLC, purified water was added to the reaction mixture. The resulting organic layer was partitioned, washed with saturated brine, dried over magnesium sulfate, and filtered. The filtrate was then concentrated under reduced pressure to give the target product as a yellow solid (7.30 kg, yield 90.7%).

$^1$H-NMR (CDCl$_3$) δ: 1.25 (3H, d, J=6.8 Hz), 3.00 (3H, s), 3.84-3.94 (1H, m), 4.11-4.19 (2H, m), 5.54 (1H, d, J=7.6 Hz), 7.74-7.80 (2H, m), 7.88-7.94 (1H, m), 8.14-8.20 (1H, m). melting point: 125-126° C.

(iii) Production of (S)-tert-butyl 3-hydroxypropyl(2-(2-nitrophenylsulfonylamide)propyl)carbamate 3-Aminopropanol (1.59 kg, 21.2 mol) and potassium carbonate (7.45 kg, 53.9 mol) were suspended in acetonitrile (24 L), followed by stirring at 70° C. To the reaction mixture was gradually added a solution of (S)—N-(1-methanesulfonyloxypropan-2-yl)-2-nitrobenzenesulfonamide (6.00 kg, 17.7 mol) in acetonitrile (48 L) at 70° C. over 2 hours. The resulting reaction mixture was further stirred for 30 minutes. After confirming the disappearance of the starting materials by TLC. The reaction mixture was allowed to cool to room temperature. The reaction mixture was poured into purified water, and then washed with petroleum ether:ethyl acetate (1:2). To the resulting aqueous layer was gradually added di-tert-butyl dicarbonate (4.00 kg, 18.3 mol) at an internal temperature of 20° C. or below over 40 minutes, followed by stirring at room temperature for 30 minutes. After confirming the disappearance of the starting materials by TLC, the insoluble materials were filtered off. The filtrate was extracted with ethyl acetate. The resulting organic layer was concentrated under reduced pressure to one-third of its volume, to which 0.5 N hydrochloric acid was added, and the precipitates were filtered off. The filtrate was separated and the resulting organic layer was washed with saturated brine, dried over magnesium sulfate, and filtered. The filtrate was concentrated under reduced pressure to give the target product as a yellow oil (7.00 kg, yield 94.7%).

$^1$H-NMR (DMSO-d$_6$, 100° C.) δ: 0.97 (3H, d, J=6.8 Hz), 1.37 (9H, s), 1.52-1.60 (2H, m), 3.06 (1H, dd, J=14.1, 7.0 Hz), 3.11 (2H, ddd, J=7.0, 7.0, 2.3 Hz), 3.18 (1H, dd, J=14.1, 7.0 Hz), 3.35 (2H, t, J=6.3 Hz), 3.58-3.68 (1H, m), 7.55 (1H, br), 7.79-7.89 (3H, m), 7.98-8.03 (1H, m).

(iv) Production of (S)-tert-butyl 4-(2-nitrophenylsulfonyl)-3-methyl-1,4-diazepane-1-carboxylate To a solution of (S)-tert-butyl 3-hydroxypropyl-2-(2-nitrophenylsulfonylamide)propylcarbamate (7.00 kg, 16.8 mol) and triphenylphosphine (4.90 kg, 18.7 mol) in tetrahydrofuran (60 L) was gradually added diisopropyl azodicarboxylate (4.60 kg, 22.7 mol) at an internal temperature of 5° C. or below over 2 hours under a nitrogen atmosphere. The resulting reaction mixture was stirred at room temperature for 7 hours. After confirming the disappearance of the starting materials by TLC, the reaction mixture was concentrated under reduced pressure. To the residue was added petroleum ether:methyl t-butyl ether (12.5:1), followed by vigorous stirring. The precipitates were filtered off and the filtrate was concentrated under reduced pressure. To the residue was added petroleum ether, followed by vigorous stirring. The precipitates were collected by filtration and dried to give the target product as a yellow solid (5.00 kg, yield 74.5%).

$^1$H-NMR (DMSO-d$_6$, 80° C.) δ: 0.89 (3H, d, J=6.8 Hz), 1.40 (9H, s), 1.65-1.72 (2H, m), 3.05-3.14 (2H, m), 3.25 (1H, ddd, J=15.6, 7.0, 7.0 Hz), 3.63 (2H, dd, J=15.6, 5.4 Hz), 3.73 (1H, ddd, J=15.6, 4.0, 4.0 Hz), 4.22-4.30 (1H, m), 7.79-7.88 (3H, m), 7.98 (1H, dd, J=7.6, 2.0 Hz). melting point: 113-114° C.

(v) Production of (S)-tert-butyl 3-methyl-1,4-diazepane-1-carboxylate

To a solution of (S)-tert-Butyl 4-(2-nitrophenylsulfonyl)-3-methyl-1,4-diazepane-1-carboxylate (2.60 kg, 6.51 mol) in acetonitrile (20 L) was added potassium carbonate (1.79 kg, 13.0 mol). To the resulting reaction mixture was gradually added thiophenol (2.15 kg, 19.5 mol) at an internal temperature of 20° C. or below over 6 hours, followed by stirring at 20° C. for 18 hours. After confirming the disappearance of the starting materials by TLC, the insoluble materials were filtered off, and the filtrate was concentrated under reduced pressure. To the residue was added ice water and the solution was acidified with 2 N hydrochloric acid until (showing) pH 3, followed by washing with ethyl acetate. The resulting aqueous layer was made alkaline with potassium carbonate until (showing) pH 9, followed by extracting with ethyl acetate. The resulting organic layer was dried over magnesium sulfate, filtered, and then concentrated under reduced pressure to give the target product as a yellow oil (1.20 kg, yield 85.7%). The chemical purity of the target product was measured to be 97.5% by gas chromatography. The product was then converted into a derivative using nosyl chloride, whose optical purity was measured to be 99.9% ee. The total yield from (S)-(+)-2-amino-1-propanol to (S)-tert-butyl 3-methyl-1,4-diazepane-1-carboxylate was 45.2%.

$^1$H-NMR (DMSO-d$_6$, 100° C.) δ: 0.94 (d, J=6.3 Hz, 3H), 1.40 (s, 9H), 1.53-1.63 (m, 1H), 1.69-1.78 (m, 1H), 2.42-2.49 (m, 1H), 2.60-2.68 (m, 1H), 2.70-2.79 (m, 1H), 2.97

(ddd, J=14.0, 4.6, 4.6 Hz, 1H), 3.17 (ddd, J=14.0, 7.7, 5.8 Hz, 1H), 3.54 (ddd, J=14.0, 6.3, 5.8 Hz, 1H), 3.60 (dd, J=14.0, 4.6 Hz, 1H).

(vi) Production of (S)-tert-butyl 4-[(4-fluoroisoquinolin-5-yl)sulfonyl]-3-methyl-1,4-diazepane-1-carboxylate To a solution of (S)-tert-butyl 3-methyl-1,4-diazepane-1-carboxylate (2.76 kg, 12.9 mol) and triethylamine (2.97 kg, 29.3 mol) in acetonitrile (45.2 kg) was added 4-fluoroisoquinoline-5-sulfonyl chloride hydrochloride (3.30 kg, 11.7 mol) and washed well with acetonitrile (6.45 kg) while ice cooling under an argon atmosphere. The resulting mixture was stirred for two hours while ice cooling. After confirming the disappearance of the starting materials by high-performance liquid chromatography (HPLC), the reaction mixture was concentrated under reduced pressure. To the residue were added ethyl acetate (74.3 kg) and a 5% sodium bicarbonate solution (66.0 kg) for extraction. The resulting organic layer was washed with water (66.0 kg) and a 20% aqueous solution of sodium chloride (33.0 kg), and then dried over anhydrous sodium sulfate. The solvent was then evaporated under reduced pressure to give the target product as a yellow amorphous product (5.18 kg, quantitative).

$^1$H-NMR (CDCl$_3$) δ: 0.82 (1.5H, d, J=6.8 Hz), 1.03 (1.5H, d, J=6.8 Hz), 1.50 (9H, s), 1.74-2.11 (2H, m), 3.15-3.39 (3H, m), 3.62-3.74 (2H, m), 3.78-3.86 (0.5H, m), 3.97-4.05 (0.5H, m), 4.17 (0.5H, dd, J=11.6, 6.5 Hz), 4.29 (0.5H, dd, J=11.2, 6.1 Hz), 7.73 (1H, t, J=7.8 Hz), 8.23 (1H, d, J=7.8 Hz), 8.56 (1H, d, J=7.1 Hz), 8.60 (1H, dd, J=24.4, 7.6 Hz), 9.15 (1H, s).

$^1$H-NMR (DMSO-d$_6$, 80° C.) δ: 0.90 (3H, d, J=6.6 Hz), 1.43 (9H, s), 1.66-1.74 (2H, m), 3.06-3.39 (3H, m), 3.59-3.76 (3H, m), 4.16-4.26 (1H, m), 7.86-7.92 (1H, m), 8.43 (1H, d, J=7.6 Hz), 8.50 (1H, d, J=8.3 Hz), 8.61 (1H, t, J=2.4 Hz), 9.31 (1H, s).

(vii) Production of (S)-4-[(4-fluoroisoquinolin-5-yl)sulfonyl]-3-methyl-1,4-diazepane To a solution of 4 N hydrochloric acid/ethyl acetate (51.7 kg) was added dropwisely a solution of (S)-tert-Butyl 4-[(4-fluoroisoquinolin-5-yl)sulfonyl]-3-methyl-1,4-diazepane-1-carboxylate (4.95 kg, 11.7 mol) in ethyl acetate (8.90 kg) and washed well with ethyl acetate (3.56 kg) while ice cooling under an argon atmosphere. The resulting mixture was stirred for 2 hours while ice-cooling, the precipitates were collected by filtration and washed with ethyl acetate (8.90 kg). The solid thus obtained was dried under reduced pressure to give a white solid. This solid was added in several portions to a 3.6% sodium hydroxide solution (41.0 kg) while ice cooling, followed by extracting twice with toluene (34.3 kg). The combined organic layers were washed with a 20% aqueous solution of sodium chloride (39.5 kg), and concentrated under reduced pressure to give the target product as a yellow amorphous product (3.53 kg, yield 93.3%). From the HPLC analytical results, the purity was found to be 99.8%. As a result of optical purity measurement, it was found to be 99.9% ee.

$^1$H-NMR (CDCl$_3$) δ: 0.91 (3H, d, J=6.6 Hz), 1.66-1.91 (2H, m), 2.54 (1H, dd, J=14.6, 8.8 Hz), 2.70 (1H, ddd, J=14.4, 9.8, 3.9 Hz), 3.19 (1H, ddd, J=13.4, 4.6, 4.6 Hz), 3.25 (1H, ddd, J=15.4, 11.6, 2.6 Hz), 3.31 (1H, dd, J=14.4, 5.9 Hz), 3.98 (1H, ddd, J=15.6, 3.4, 3.4 Hz), 3.99-4.09 (1H, m), 7.73 (1H, t, J=7.9 Hz), 8.22 (1H, dq, J=8.2, 1.1 Hz), 8.57 (1H, d, J=4.9 Hz), 8.83 (1H, dd, J=7.6, 1.2 Hz), 9.15 (1H, s).

Here, as can be seen from the aforementioned sections (vi) and (vii), the two steps for synthesizing (S)-4-[(4-fluoroisoquinolin-5-yl)sulfonyl]-3-methyl-1,4-diazepane from (S)-tert-butyl 3-methyl-1,4-diazepane-1-carboxylate were accomplished with a total yield of 93.3%, showing that the target product was successfully synthesized with a remarkably higher yield than what can be achieved by the method described in the aforementioned Patent Document 1. It should be noted that the product was not produced with a sufficiently high yield according to the method described in Patent Document 1. Namely, in Example 1, the total yield was 19.2% over two steps.

Example 2

Production of (S)-tert-butyl 4-(2-nitrophenylsulfonyl)-3-methyl-1,4-diazepane-1-carboxylate (S)-tert-Butyl 4-(2-nitrophenylsulfonyl)-3-methyl-1,4-diazepane-1-carboxylate was produced by a different route from that used in the aforementioned Example 1.

Production of (S)—N-(1-(3-hydroxypropylamino)-propan-2-yl)-2-nitrobenzenesulfonamide To a solution of 3-Aminopropanol (5.00 kg, 66.6 mol) in acetonitrile (35 L) was added (S)—N-(1-methanesulfonyloxypropan-2-yl)-2-nitrobenzenesulfonamide (7.00 kg, 20.7 mol) was added at an internal temperature of 10° C. to 20° C. The reaction mixture was further stirred for 16 hours. After confirming the disappearance of the starting materials by TLC, the mixture was concentrated under reduced pressure. To the residue was added water. The resulting solution was acidified with 6 N hydrochloric acid until pH 4, and the insoluble materials were filtered off. The filtrate was made alkaline by adding potassium carbonate until pH 9 and extracted with ethyl acetate. The resulting organic layer was washed with saturated brine, dried over anhydrous sodium sulfate, and filtered. The filtrate was concentrated under reduced pressure to give the target product as a pale yellow oil (6.10 kg, 92.8%).

$^1$H-NMR (CDCl$_3$) δ: 1.11 (3H, d, J=6.8 Hz), 1.58-1.70 (2H, m), 2.61 (1H, dd, J=12.5, 7.4 Hz), 2.68 (1H, dd, J=12.5, 4.6 Hz), 2.76 (2H, t, J=6.0 Hz), 3.53-3.62 (1H, m), 3.69-3.78 (2H, m), 7.71-7.78 (2H, m), 7.84-7.89 (1H, m), 8.14-8.19 (1H, m).

Production of (S)-2-methyl-1-(2-nitrophenylsulfonyl)-1,4-diazepane hydrochloride To a solution of (S)—N-(1-(3-hydroxypropylamino)-propan-2-yl)-2-nitrobenzenesulfonamide (6.10 kg, 19.2 mol) and triphenylphosphine (6.50 kg, 24.8 mol) in tetrahydrofuran (35 L) was gradually added diisopropyl azodicarboxylate (5.20 kg, 25.7 mol) at an internal temperature of 5° C. or below over 4 hours under a nitrogen atmosphere. The resulting reaction mixture was stirred at room temperature for 7 hours. After confirming the disappearance of the starting materials by TLC, the mixture was concentrated under reduced pressure. To the residue was added ethyl acetate, and the resulting solution was acidified with 6 N hydrochloric acid until pH 4. The solid precipitates were collected by filtration to give the target product as a white solid (2.76 kg, yield 42.8%).

$^1$H-NMR (CDCl$_3$) δ: 0.99 (3H, d, J=6.8 Hz), 1.64-1.79 (2H, m), 2.51 (1H, dd, J=15.1, 9.3 Hz), 2.68 (1H, ddd, J=15.1, 9.3, 4.4 Hz), 3.08 (1H, ddd, J=15.1, 4.4, 4.4 Hz), 3.20 (1H, ddd, J=15.1, 9.3, 4.4 Hz), 3.26 (1H, dd, J=15.1, 4.4 Hz), 3.84 (1H, ddd, J=15.1, 4.4, 4.4 Hz), 4.08-4.18 (1H, m), 7.59-7.71 (3H, m), 8.13-8.19 (1H, m).

Further, (S)-2-methyl-1-(2-nitrophenylsulfonyl)-1,4-diazepane was also produced by the following method in which cation exchange resin was used as a purification procedure.

To a solution of (S)—N-(1-(3-hydroxypropylamino)-propan-2-yl)-2-nitrobenzenesulfonamide (627 mg, 1.98 mmol) and triphenylphosphine (624 mg, 2.38 mmol) in tetrahydrofuran (5 mL) was gradually added diisopropyl azodicarboxylate (0.47 mL, 2.38 mmol) at an internal temperature of 5° C. or below over 10 minutes under a nitrogen atmosphere. The resulting reaction mixture was stirred at room temperature for 16 hours. After confirming the disappearance of the starting materials by TLC, to the reaction mixture was added Amberlyst 15™ (1.6 g) (the product of The Dow Chemical Company) and the resulting suspension was gently shaken for 20 hours. The resin was filtered and washed with tetrahydrofuran, followed by eluting with ammonia-methanol. The filtrate was concentrated to give the target product as a pale brown amorphous product (557 mg, yield 93.9%). When DIAION™ RCP160M (1.6 g) (the product of Mitsubishi Chemical Corporation) was used in place of Amberlyst 15™ (1.6 g), the target product was obtained as a pale brown amorphous product with a yield of 84.3%. Further, when DOWEX™ MAC-3 (1.6 g) (the product of The Dow Chemical Company) was used in place of Amberlyst 15™ (1.6 g), the target product was obtained as a pale brown amorphous product with a yield of 88.6%.

Production of (S)-tert-butyl 4-(2-nitrophenylsulfonyl)-3-methyl-1,4-diazepane-1-carboxylate To a solution of (S)-2-methyl-1-(2-nitrophenylsulfonyl)-1,4-diazepane hydrochloride (2.70 kg, 8.04 mol) in a mixture of ethanol (12 L) and water (12 L) was added potassium carbonate (1.50 kg, 10.9 mol). The resulting reaction mixture was cooled to 5° C. or below, and gradually added di-tert-butyl dicarbonate (2.00 kg, 9.16 mol). The reaction mixture was stirred at 5° C. for 5 hours. After confirming the disappearance of the starting materials by TLC, the reaction mixture was concentrated under reduced pressure to give the target product as a yellow solid (2.80 kg, yield 87.2%).

$^1$H-NMR (DMSO-$d_6$, 80° C.) δ: 0.89 (3H, d, J=6.8 Hz), 1.40 (9H, s), 1.65-1.72 (2H, m), 3.05-3.14 (2H, m), 3.25 (1H, ddd, J=15.6, 7.0, 7.0 Hz), 3.63 (2H, dd, J=15.6, 5.4 Hz), 3.73 (1H, ddd, J=15.6, 4.0, 4.0 Hz), 4.22-4.30 (1H, m), 7.79-7.88 (3H, m), 7.98 (1H, dd, J=7.6, 2.0 Hz). melting point: 113-114° C.

Comparative Example 1

Production of (S)-tert-butyl 3-methyl-1,4-diazepane-1-carboxylate (S)-tert-Butyl 3-methyl-1,4-diazepane-1-carboxylate was produced by the method of the aforementioned Patent Document 1.
(i) Production of (S)-benzyl(1-hydroxypropan-2-yl)carbamate To a solution of (S)-(+)-2-amino-1-propanol (200 g, 2.66 mol) in purified water (400 mL) was added sodium bicarbonate (246 g, 2.93 mol). To this mixture was added benzyl chloroformate (500 g, 2.93 mol) in tetrahydrofuran (800 mL) at an internal temperature of 20° C. or below. Subsequently, the resulting reaction mixture was stirred at room temperature for 16 hours. After confirming the disappearance of the starting materials by TLC, the reaction mixture was then extracted with ethyl acetate. The organic layer was washed with 0.5 N hydrochloric acid, saturated aqueous sodium bicarbonate, and saturated brine, and then dried over anhydrous sodium sulfate. The resulting solution was filtered and concentrated under reduced pressure. The residue was crystallized from petroleum ether to give the target product as a white solid (403 g, yield 72.3%).

$^1$H-NMR (CDCl$_3$) δ: 1.17 (3H, d, J=6.8 Hz), 2.31 (1H, brs), 3.48-3.57 (1H, m), 3.62-3.71 (1H, m), 3.78-3.90 (1H, m), 4.90 (1H, s), 5.10 (2H, s), 7.29-7.39 (5H, m).

(ii) Production of (S)-2-(benzyloxycarbonylamino)propyl methanesulfonate

A solution of (S)-benzyl(1-hydroxypropan-2-yl)carbamate (400 g, 1.91 mol) and triethylamine (270 g, 2.67 mol) in methylene chloride (2.4 L) was cooled to 0° C. To this mixture was added methanesulfonyl chloride (263 g, 2.30 mol) at an internal temperature of 5° C. or below. Subsequently, the resulting reaction mixture was stirred at room temperature for 16 hours. After confirming the disappearance of the starting materials by TLC, to the reaction mixture was added purified water. The resulting organic layer was partitioned, washed with saturated brine, dried over magnesium sulfate, and filtered. The filtrate was concentrated under reduced pressure to give the target product as a yellow solid (519 g, yield 94.5%).

$^1$H-NMR (CDCl$_3$) δ: 1.26 (3H, d, J=6.8 Hz), 2.97 (3H, s), 4.00-4.11 (1H, m), 4.12-4.20 (1H, m), 4.21-4.30 (1H, m), 4.89 (1H, br s), 5.10 (2H, s), 7.29-7.39 (5H, m).

(iii) Production of (S)-6-benzyloxycarbonylamino-4-(tert-butoxycarbonyl)-4-azaheptan-1-ol (S)-2-(Benzyloxycarbonylamino)propyl methanesulfonate (468 g, 1.63 mol) and 3-aminopropanol (672 g, 8.96 mol) were suspended in tetrahydrofuran (2.4 L), followed by stirring at 80° C. for 16 hours. After confirming the disappearance of the starting materials by TLC, the resulting mixture was allowed to cool to room temperature. To the reaction mixture was added purified water, followed by extracting with methylene chloride. The resulting organic layer was washed with saturated brine. To the organic layer was added di-tert-butyl dicarbonate (359 g, 1.64 mol) at an internal temperature of 35° C. or below, followed by stirring at room temperature for 3 hours. After confirming the disappearance of the starting materials by TLC, the organic layer was washed with 0.5 N hydrochloric acid, saturated aqueous sodium bicarbonate, and saturated brine, and then dried over anhydrous sodium sulfate. The resulting solution was filtered and then concentrated under reduced pressure. The residue was purified by silica gel chromatography (20 to 40% ethyl acetate-petroleum ether) to give the target product as a pale yellow oil (380 g, yield 63.7%).

$^1$H-NMR (CDCl$_3$) δ: 1.15 (3H, d, J=6.8 Hz), 1.44 (9H, d, J=11.7 Hz), 1.62-1.80 (2H, m), 2.89-3.17 (1H, m), 3.22-3.66 (5H, m), 3.83-4.00 (1H, m), 4.85 (1H, br s), 5.08 (2H, s), 7.27-7.41 (5H, m).

(iv) Production of (S)-6-benzyloxycarbonylamino-4-(tert-butoxycarbonyl)-4-azaheptyl methanesulfonate (S)-6-Benzyloxycarbonylamino-4-(tert-butoxycarbonyl)-4-azaheptan-1-ol (380 g, 1.04 mol) and triethylamine (147 g, 1.45 mol) were dissolved in methylene chloride (5.0 L). The resulting solution was cooled to 0° C., to which a solution of methanesulfonyl chloride (143 g, 1.25 mol) in methylene chloride (0.1 L) was added at an internal temperature of 5° C. or below. Subsequently, the reaction mixture was stirred at room temperature for 16 hours. After confirming the disappearance of the starting materials by TLC, purified water was added to the reaction mixture for extraction. The resulting organic layer was washed with 0.5 N hydrochloric acid, saturated aqueous sodium bicarbonate, and saturated brine, and then dried over anhydrous sodium sulfate. The resulting mixture was filtered and concentrated under reduced pressure to give the target product as a yellow oil (425 g, yield 92.0%). Despite the fact that the compound thus obtained was refrigerated, the degradation reaction proceeded, revealing that this compound was unstable.

$^1$H-NMR (CDCl$_3$) δ: 1.14 (3H, d, J=6.8 Hz), 1.44 (9H, s), 1.89-2.06 (2H, m), 3.01 (3H, s), 3.08-3.62 (4H, m), 3.82-3.97 (1H, m), 4.16-4.29 (2H, m), 5.07 (2H, s), 7.28-7.40 (5H, m).

(v) Production of (S)-1-benzyl 4-tert-butyl 2-methyl-1,4-diazepane-1,4-dicarboxylate To a solution of (S)-6-Benzyloxycarbonylamino-4-(tert-butoxycarbonyl)-4-azaheptyl methanesulfonate (425 g, 0.956 mol) in dimethyl sulfoxide (1.6 L) was added 60% sodium hydride (76.5 g, 1.91 mol) at an internal temperature of 25° C. or below, followed by stirring at room temperature for 2 hours. After confirming the disappearance of the starting materials by TLC, the reaction mixture was poured into water, followed by extracting with ethyl acetate. The resulting organic layer was washed with saturated brine, 0.5 N hydrochloric acid, saturated aqueous sodium bicarbonate, and saturated brine in this order, and then dried over anhydrous sodium sulfate. The resulting solution was filtered and concentrated under reduced pressure. The residue was purified by flash silica gel chromatography (14% ethyl acetate-petroleum ether) to give the target product as a pale yellow oil (199 g, containing about 30 g of mineral oil, yield 50.4%).

$^1$H-NMR (DMSO-d$_6$, 100° C.) δ: 0.98 (3H, d, J=6.8 Hz), 1.36 (9H, s), 1.52-1.70 (2H, m), 2.92-2.99 (1H, m), 2.92 (1H, dd, J=14.1, 10.3 Hz), 2.99 (1H, ddd, J=14.1, 10.3, 2.5 Hz), 3.62-3.71 (1H, m), 3.78 (1H, dd, J=14.1, 6.1 Hz), 3.82-3.90 (1H, m), 4.29-4.40 (1H, m), 5.03 (1H, d, J=12.7 Hz), 5.07 (1H, d, J=12.7 Hz), 7.25-7.36 (5H, m).

(vi) Production of (S)-tert-butyl 3-methyl-1,4-diazepane-1-carboxylate

To a solution of (S)-1-benzyl 4-tert-butyl 2-methyl-1,4-diazepane-1,4-dicarboxylate (189 g, containing about 28.5 g of mineral oil, 0.461 mol) in methanol (1.0 L) was added 10% palladium/carbon (19.0 g) under a nitrogen atmosphere. The inside of the container was replaced by hydrogen gas, followed by stirring at room temperature for 19 hours. After confirming the disappearance of the starting materials by TLC, the resulting reaction mixture was filtered and concentrated under reduced pressure. To the residue was dissolved in ethyl acetate. The solution was extracted with an aqueous solution of citric acid. The resulting aqueous layer was made alkaline until pH 9. The aqueous layer was extracted with ethyl acetate. The organic layer was washed with saturated brine, and then dried over anhydrous sodium sulfate. The resulting solution was filtered and concentrated under reduced pressure to give the target product as a pale yellow oil (60.0 g, 60.7%). The chemical purity of the target product was measured to be 95.0% by gas chromatography. The product was then converted into a derivative using nosyl chloride, whose optical purity was measured to be 97.5% ee. The total yield from (S)-(+)-2-amino-1-propanol to (S)-tert-butyl 3-methyl-1,4-diazepane-1-carboxylate was 12.21%.

$^1$H-NMR (DMSO-d$_6$, 100° C.) δ: 0.94 (d, J=6.3 Hz, 3H), 1.40 (s, 9H), 1.53-1.63 (m, 1H), 1.69-1.78 (m, 1H), 2.42-2.49 (m, 1H), 2.60-2.68 (m, 1H), 2.70-2.79 (m, 1H), 2.97 (ddd, J=14.0, 4.6, 4.6 Hz, 1H), 3.17 (ddd, J=14.0, 7.7, 5.8 Hz, 1H), 3.54 (ddd, J=14.0, 6.3, 5.8 Hz, 1H), 3.60 (dd, J=14.0, 4.6 Hz, 1H).

Test Example 1

Calculation of the Conversion Ratio from the Starting Material to the Product

In each of the solvents shown in the following Table 2, (S)-tert-butyl 3-methyl-1,4-diazepane-1-carboxylate (45 mg, 0.212 mmol) and triethylamine (63 µL, 0.443 mmol) were dissolved in each solvent under an argon atmosphere, followed by stirring while ice cooling (2 to 8° C.). To each of the resulting reaction mixtures was added 4-fluoroisoquinoline-5-sulfonyl chloride hydrochloride (50 mg, 0.177 mmol). The resulting mixture was stirred while ice cooling (2 to 8° C.) from the start of the reaction up to 3 hours, and at room temperature for another 14 hours. During this time, 20 µL of each reaction mixture was sampled after 0.5, 1, 2, 3, and 17 hours and quenched with a saturated ammonia/methanol solution (0.5 mL). The resulting quenched solution was diluted with acetonitrile (1.5 mL) and used as a sample for HPLC measurement.

The staring material, i.e., 4-fluoroisoquinoline-5-sulfonyl chloride hydrochloride, is converted into 4-fluoroisoquinoline-5-sulfonamide by a saturated ammonia/methanol solution. The ratio between this 4-fluoroisoquinoline-5-sulfonamide and the product, i.e., (S)-tert-butyl 4-[(4-fluoroisoquinolin-5-yl)sulfonyl]-3-methyl-1,4-diazepane-1-carboxylate, was measured under the following HPLC conditions, and the conversion ratio from the starting material to the product in each solvent was calculated. The calculation results thus obtained are shown in Table 2. It should be noted that the retention time of 4-fluoroisoquinoline-5-sulfonamide was about 4.7 minutes, and the retention time of (S)-tert-butyl 4-[(4-fluoroisoquinolin-5-yl)sulfonyl]-3-methyl-1,4-diazepane-1-carboxylate was about 8.3 minutes.

HPLC Measurement Conditions

Detector: A ultraviolet absorption photometer (wavelength 220 nm)
Column: Inertsil ODV-3V (diameter 4.6 mm×150 mm)
Column temperature: A constant temperature of around 40° C.
Mobile phase A: Water
Mobile phase B: Acetonitrile
Flow rate: 1.0 mL per minute
Time span of measurement: 10 minutes
Mobile phase feed: The mobile phase was ratio was changed the mixed ratios of the mobile phase A and mobile phase B stepwise as follows;

TABLE 1

| Time after injection (minutes) | Mobile phase A (%) | Mobile phase B (%) |
|---|---|---|
| 0~6 | 90 → 20 | 10 → 80 |
| 6~10 | 20 | 80 |

TABLE 2

| | Conversion ratio (%) | | | | |
|---|---|---|---|---|---|
| Solvent | 0.5 h | 1 h | 2 h | 3 h | 17 h |
| Dimethyl sulfoxide | 52.3 | 85.4 | 99.7 | 99.9 | 99.9 |
| Acetonitrile | 77.3 | 89.3 | 99.0 | 99.0 | 99.7 |
| N,N-Dimethylformamide | 96.4 | 99.5 | 99.9 | 99.9 | 99.9 |
| N-Methylpyrrolidone | 94.4 | 99.2 | 99.9 | 99.9 | 99.9 |

TABLE 2-continued

| Solvent | Conversion ratio (%) | | | | |
|---|---|---|---|---|---|
| | 0.5 h | 1 h | 2 h | 3 h | 17 h |
| Acetone | 33.4 | 50.6 | 67.5 | 80.5 | 98.1 |
| Methylene chloride | 9.2 | 16.5 | 29.6 | 42.0 | 98.9 |
| Tetrahydrofuran | 1.0 | 2.0 | 3.6 | 5.0 | 50.1 |
| Dimethoxyethane | 1.1 | 2.2 | 4.5 | 11.5 | 94.7 |
| Ethyl acetate | 1.2 | 2.3 | 4.6 | 6.4 | 57.2 |
| Cyclopentyl methyl ether | 0.3 | 0.4 | 0.6 | 1.0 | 17.8 |
| Chloroform | 2.1 | 5.0 | 9.3 | 13.0 | 86.4 |
| Toluene | 0.3 | 0.5 | 0.8 | 1.3 | 16.5 |
| Dioxane | 16.2 | 26.5 | 49.5 | 66.1 | 81.4 |
| t-Butyl methyl ether | 0.2 | 0.4 | 0.8 | 4.0 | 37.2 |

As is apparent from Table 2, the conversion ratios in the reactions of the compound (II) with the compound (III) greatly vary depending on the reaction solvent used. Among various kinds of solvents, particularly favorable conversion ratios are obtained when a nitrile solvent, an amide solvent, a sulfoxide solvent, and a urea solvent are used. Further, particularly excellent conversion ratios are obtained when dimethylsulfoxide, acetonitrile, N,N-dimethylformamide, and N-methylpyrrolidone are used, and regardless of a reaction temperature as low as 0 to 10° C., the reactions have almost been completed in about 2 hours. Also, considering post-reaction treatment such as removal of solvents, acetonitrile is particularly preferable.

INDUSTRIAL APPLICABILITY

According to the present invention, the target product, i.e., a compound represented by the aforementioned formula (I) or a salt thereof, which is useful for preventing and treating cerebrovascular disorders such as cerebral infarction, cerebral hemorrhage, subarachnoid hemorrhage, and cerebral edema, particularly for preventing and treating glaucoma, can be produced at high yield and high purity even on a large scale without imposing a negative impact on the environment and requiring complex silica gel column chromatographic purification or purification consisting of recrystallization of crystalline salts such as organic acid salts. The method of the present invention is excellent for a large scale producing the compound (I) or a salt thereof at high purity and high yield in an easy and simple way without requiring complex operations and performing a number of steps.

The invention claimed is:

1. A method for producing a compound of formula (II-3) or a salt thereof:

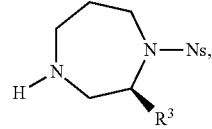

(II-3)

the method comprising reacting a compound of formula (VI):

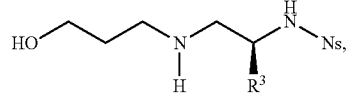

(VI)

in a solvent in a presence of a phosphine reagent and an azo reagent, wherein $R^3$ is a $C_{1-4}$ alkyl group and Ns is a nosyl group.

2. The method according to claim 1, wherein the phosphine reagent is triphenylphosphine and the azo reagent is diisopropyl azodicarboxylate.

3. The method according to claim 1, further comprising purifying with a cation exchange resin.

* * * * *